United States Patent
Giammona et al.

(10) Patent No.: US 9,410,000 B2
(45) Date of Patent: Aug. 9, 2016

(54) METHOD TO PRODUCE HYALURONIC ACID FUNCTIONALIZED DERIVATIVES AND FORMATION OF HYDROGELS

(71) Applicants: Gaetano Giammona, Palermo (IT); Fabio Palumbo, Trabia (IT); Giovanna Pitarresi, Palermo (IT)

(72) Inventors: Gaetano Giammona, Palermo (IT); Fabio Palumbo, Trabia (IT); Giovanna Pitarresi, Palermo (IT)

(73) Assignee: UNIVERSITA' DEGLI STUDI DI PALERMO, Palermo (IT)

( * ) Notice: Subject to any disclaimer, the term of this patent is extended or adjusted under 35 U.S.C. 154(b) by 127 days.

(21) Appl. No.: 14/507,474

(22) Filed: Nov. 13, 2014

(65) Prior Publication Data

US 2015/0183891 A1    Jul. 2, 2015

Related U.S. Application Data

(62) Division of application No. 13/131,098, filed as application No. PCT/EP2009/066060 on Nov. 30, 2009, now Pat. No. 8,858,999.

(30) Foreign Application Priority Data

Nov. 28, 2008 (IT) .............. RM2008A0636

(51) Int. Cl.
    C08B 37/08    (2006.01)
    B23K 9/10    (2006.01)

(52) U.S. Cl.
    CPC ............... *C08B 37/0072* (2013.01); *B23K 9/10* (2013.01)

(58) Field of Classification Search
    CPC combination set(s) only.
    See application file for complete search history.

(56) References Cited

U.S. PATENT DOCUMENTS

2007/0224277 A1    9/2007    Borbely et al.

FOREIGN PATENT DOCUMENTS

| EP | 1666518 A1 | 6/2006 |
|----|------------|--------|
| WO | 9524429 | 9/1995 |
| WO | 03002125 | 9/2003 |
| WO | 2007083870 A1 | 7/2007 |
| WO | 2010061005 A1 | 6/2010 |

OTHER PUBLICATIONS

Notification of Transmittal of the International Search Report and the Written Opinion of the International Searching Authority, or the Declaration of International Application No. PCT/EP2009/066060, dated Mar. 29, 2010.
Notification of Transmittal of the International Preliminary Report on Patentability of International Application No. PCT/EP2009/066060, dated Mar. 1, 2011.
Pitaressi et al., J. Biomedical Medicals Research Part A, Wiley InterScience (Jul. 6, 2007).
Pitaressi et al., Biomacromolecules 2006, 7, 1302-1310.

*Primary Examiner* — Michael G Hartley
*Assistant Examiner* — Robert Cabral
(74) *Attorney, Agent, or Firm* — Abelman, Frayne & Schwab

(57) ABSTRACT

In this invention a two steps procedure is described useful to insert functional groups to the hyaluronic acid (HA), through the formation, in organic solvent, of a particular active group on hydroxyl groups of HA and subsequent substitution, on the inserted active group, with a pendant portion containing at least in its terminal portion a nucleophilic functional group, $NH_2$—R.
The group inserted by nucleophilic substitution can contain in another its terminal portion a further nucleophilic functional group, in a way to be easily exploitable to further chemical functionalizations, such as an example to obtain the methacrylation of HA functional groups, to obtain photocrosslinkable derivatives.
Both direct derivatives of the proposed process and those obtained by the further functionalization can be employed to produce hydrogels.

20 Claims, 4 Drawing Sheets

METHOD TO PRODUCE HYALURONIC ACID FUNCTIONALIZED DERIVATIVES AND FORMATION OF HYDROGELS

CROSS-REFERENCE TO RELATED APPLICATIONS

This application is a Divisional Application of Ser. No. 13/131,098, filed 25 May, 2011, which is a National Phase of PCT/EP2009/066060, filed 30 Nov. 2009, which claims priority from Italian Application No. RM 2008A000636, filed 28 Nov. 2008, the specifications of which are all incorporated herein by reference.

FIELD OF THE INVENTION

This invention concerns a procedure for the production of functionalized hyaluronic acid derivatives and relative hydrogels. More in particular, this invention concerns a two steps methodology useful to insert functional groups onto hyaluronic acid, through the formation of a specific active group on hydroxyl groups of hyaluronic acid and the subsequent substitution of the inserted active group, with a pendent portion containing as terminal portion at least a nucleophilic functional group. The group inserted by nucleophilic substitution can contain as other terminal portion another nucleophilic functional group exploitable for further chemical functionalizations, in particular to favour crosslinking of hyaluronic acid chains producing hydrogels.

PRIOR ART

Hyaluronic acid (HA) is the most abundant not sulphated glycosaminoglycan present in the extracellular matrix of all tissues; HA is a polysaccharide constituted by repetitive units of D-glucuronic acid (GlcUA) and N-acetyl-D-glucosamine (GlcNAc) whose chemical structure can be represented by the following formula showing two consecutive repetitive units (the number n of repetitive units could be such to determine a molecular weight comprised between 50000 and several million of Dalton).

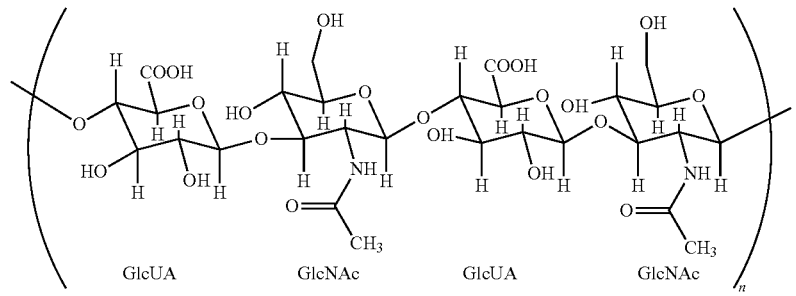

Hyaluronic acid actively participates to a number of important biological processes such as cell mobility, cell differentiation, wound healing. In particular HA plays a key structural role in the organization of the cartilage extracellular matrix taking place to the formation of the more abundant proteoglycan, i.e. aggrecan.

Hyaluronic acid with high molecular weight is used in viscosurgery and viscosupplementation and it is used in ophthalmic field and to reduce pain in osteoarthritis as lubricating that can be applied through intra-articular injections.

Recently several functional or crosslinked HA derivatives have been produced as films or sponges to be applied on the wounds, where this product has healing tissue properties.

In the tissue engineering field—emerging subject concerning the development of useful technologies to obtain regeneration or complete replacement of damaged human tissues—the HA has been largely employed for the production of three-dimensional porous structures known as scaffolds. These matrices improve tissue cells growing and differentiation to favour tissue regeneration and reconstruction.

For such applications HA is useful when suitably substituted to obtain hydrogels. As known hydrogels are constituted by natural or synthetic polymers or their derivatives or by combinations of natural and synthetic polymers, which molecules interact as results of Van der Waals interactions, hydrogen bonding, electrostatic or chemical linkages, therefore hydrogels are networks of hydrophilic polymers able to absorb water until hundreds times their dry weight. Considering their hydrophilic properties and their potential biocompatibility, hydrogels receive a growing interest for pharmaceutical and pharmaceutical-biomedical applications.

The chemical functionalization of the polysaccharidic HA structure by inserting pendant functional groups has the objective to obtain pharmaceutical devices to prolong drug release (drug delivery systems); in such systems the drug is physically or chemically linked to the polysaccharide carrier, and it is released following manners and times able to improve drug bioavailability.

Considering the great interest toward mentioned pharmaceutical, biomedical and cosmetic hyaluronic acid applications, it is evident the high demand of new chemical strategies to allow new and simpler HA modifications. These new derivatives can then be employed to fit the various possible applications.

In the past, several chemical modifications of hyaluronic acid concerning its hydroxyl and carboxyl functionalities and several HA derivatives for application in biomedical or pharmaceutical field have been described.

As example the U.S. Pat. No. 4,582,865 (Balasz et. al by Biomatrix Inc.) describes the HA cross-linking by reaction with divinylsulfone in highly basic conditions. European Patent Application EP 0216453 (Fidia S.p.A.) describes esterifications of hyaluronate salts with alkyl halides in polar aprotic solvents. Such derivatives have found large applications in pharmaceutical field, such as scaffolds for tissue engineering and as devices to control drug release. These ester HA derivatives have modified physicochemical characteristics such as increased solubility in organic solvents, such as dimethylsulfoxide that improve industrial performances to obtain fibres, porous scaffolds and films.

Recently other different chemical strategies have been proposed to obtain hyaluronic acid functionalization with functional pendant chains, employing reactions both on carboxyl groups of the glucuronic moiety and on hydroxyl groups of the repetitive units. In particular several papers describe carbodiimide chemistry (employing compounds having formula $R^1$—N=C=N—$R^2$) to obtain chemical functionalization of D-glucuronic moiety of HA.

As example Prestwich, Poyani et al. employed water soluble carbodiimides to insert hydrazide pendant chains on the hyaluronan backbone (U.S. Pat. No. 5,502,081 of Prestwich et al. by The Research Foundation of State University of New York; U.S. Pat. No. 5,616,568 of T. Pouyany et al.; T. Pouyany, G. D. Prestwich Functionalized Derivatives of Hyaluronic Acid Oligosaccharides: Drug Carriers and Novel Biomaterials, *Bioconjugate Chem.*, 1994, 5, 339-347). In these examples hyaluronic acid carboxyl groups react with bi-functional molecules having general formula $H_2N$—NH—CO-A-CO—$NHNH_2$ where A is a generic spacing group, producing functionalized hyaluronic acid derivatives bearing pendant hydrazide groups having formula HA-CONH—NH—CO-A-CO—NH—$NH_2$. Following the same research line, Vercruysse et al. (Vercruysse et al., "Synthesis and in Vitro Degradation of New Polyvalent Hydrazide Cross-Linked Hydrogels of Hyalyronic Acid, *Bioconjugate Chem.*, 1997, 8, 686-694) described how to functionalize hyaluronic acid using molecules bearing more than two hydrazide terminal groups, allowing a crosslinking of the starting polysaccharide then producing hydrogels.

Aeschlimann et al. (U.S. Pat. No. 6,630,457 of Aeschlimann et al. by Othogene LLC corresponding to European patent N. EP 1757314) modified the method of activation of the carboxyl group of HA proposed by Pouyani, by combining to the employ of water soluble carbodiimides the use of nucleophilic activators such as hydroxysuccinimides and hydroxytriazoles. In particular the disclosed method deals with the introduction of new functional groups on the HA backbone by first activating its carboxylic groups producing intermediate ester groups, then substituting these ester leaving groups using molecules containing a good nucleophilic group in one side and a chemically protected functional group in another side. In this way, the HA activated intermediates are more stable and then the following functionalization by bifunctional nucleophilic molecules is more selective. In such manner amine and aldehyde HA derivatives have been produced suitable for subsequent crosslinking, thus obtaining biocompatible HA based hydrogels.

Moreover the patent application WO 02/098923 proposed by Eurand Pharmaceuticals Ltd, inventors Mariotti et al., shows the methods to produce functionalized HA derivatives where its hydroxyl groups are esterified or carbamoylated (HA-O—CONH—) and the carboxyl groups are totally or partially esterified with alcohols. Such carbamoylated hydroxyl groups are obtained reacting the polysaccharide with alkyl, aryl or arylalkyl isocyanates (R—N=C=O). In such manner carbamoylated and esterified HA derivatives have been obtained to be applied as stationary phases for chromatographic analysis.

Similarly to how described by Mariotti et al., Chen Juihsiang et al., in the patent EP 1538166 (proposed by Industrial Technology Research Institute) describes the production of HA derivatives bearing as pendant chains hydrophobic, hydrophilic and amphyphilic polymers, obtained by reaction between the polysaccharide and isocyanates derivatives of the same polymers.

The last two patents cited describe the formation of carbamic HA derivative on the primary hydroxyl groups of the disaccharide repetitive units, by performing a reaction using polar aprotic solvent soluble HA salts and reactive isocyanates. In this case, the hydroxyl groups of the hyaluronic acid were functionalized in a single step reaction, producing then a carbamic linkage (—O—CO—NH—, also known as urethanic linkage) between hyaluronic acid and the new pendant functionality; such functionalization can be then described using the following general formula (HA-O—CO—NH—R) where R could be hydrophilic, lipophilic or amphyphilic chain. However the cited methodologies suffer of the inconvenient that the functionalization is restricted only to isocyanates derivatives that have to be employed as starting reactants.

Considering the methodologies described above, this invention has the aim to disclose a new method for the production of functionalized HA derivatives exploitable for the production of crosslinked hydrogels or as useful intermediates to obtain further functionalization, both in aqueous and organic solvents. Further aim of this invention is to disclose methodologies where these functional HA derivatives can be easily exploited for the production of new hydrogels.

SUMMARY OF THE INVENTION

Following this aim, according to the present invention, a versatile chemical method has been found to obtain HA functional derivatives in such a way which does not involve in the chemical reaction the carboxyl groups of the hyaluronic acid glucuronic moieties. This method involves a two steps procedure, where the first step is the introduction of a chemical active portion on at least one hydroxyl group of hyaluronic acid to give an active intermediate, and where in the second step said active intermediate reacts with a reactive nucleophile; said reactive nucleophile bearing at least one primary amino group. The consecutive application of the two steps procedure generates the formation of at least one carbamic group (—O—CO—NH—) linked to the HA backbone through at least one of its hydroxyl groups.

In particular in the first step of the method, specific activating molecules such as the well known and commercially available bis(4-nitrophenyl carbonate) or the chloro nitrophenyl carbonate are employed to insert nitrophenoxycarbonyl groups ($NO_2$-Ph-O—CO—) on HA hydroxyl groups (primary and/or secondary); in the second step the good leaving group inserted (nitrophenoxyle) is substituted by a nucleophilic molecule having general formula $NH_2$—R. Such nucleophilic molecule should contain at least one amine primary group, and R represents a $NH_2$, an alkylamino group, an alkylic chain, an arylalkyl chain, a polyacrylic chain, a polyoxyethylene chain or more generally any molecule with low (as example a drug) or high molecular weight (as example a polymer, a protein etc); preferably said molecule with low or high molecular weight is biocompatible and soluble either in organic solvents or in aqueous medium.

According to this invention, it is possible to obtain a new carbamic linkage, by a two phases reaction, on the primary and/or secondary hydroxyl groups of HA, employing the opportune intermediate of activation. In particular, the reactive bis(4-nitrophenyl carbonate) has been employed to generate a reactive nitrophenylcarbonate derivative on the HA, easily reactive toward nucleophilic molecules preferably bearing amino or hydrazide functionalities.

The pendant chain inserted on the second step of the procedure, in case of need, can bear at least another functional group still available for further chemical functionalizations performed in organic or aqueous medium, reacting with molecules bearing other functional groups, in particular chemical groups able to allow a crosslinking reaction.

The method disclosed can be employed to produce HA derivatives bearing new amine or hydrazide chemical functionalities or to produce HA derivatives bearing hydrophilic or lipophilic pendant chains.

In such manner a wide variety of chemical functional groups commercially available can be linked to HA through its hydroxyl groups (primary and/or secondary). Moreover following this procedure it is possible further functionalize such amino and hydrazide derivatives also in organic environment: in particular the tetrabutylammonium salts (TBA) of such amino or hydrazide HA derivatives can be employed for further functionalization. In general such further functionalization can be performed in both aqueous and organic medium, in particular polar aprotic solvents such as dimethylsulfoxide, dimethylformamide and dimethylacetamide and their mixtures.

BRIEF DESCRIPTION OF THE FIGURES

Some experimental results are illustrated in the following drawings, where.

DETAILED DESCRIPTION OF THE INVENTION

Figure 1:
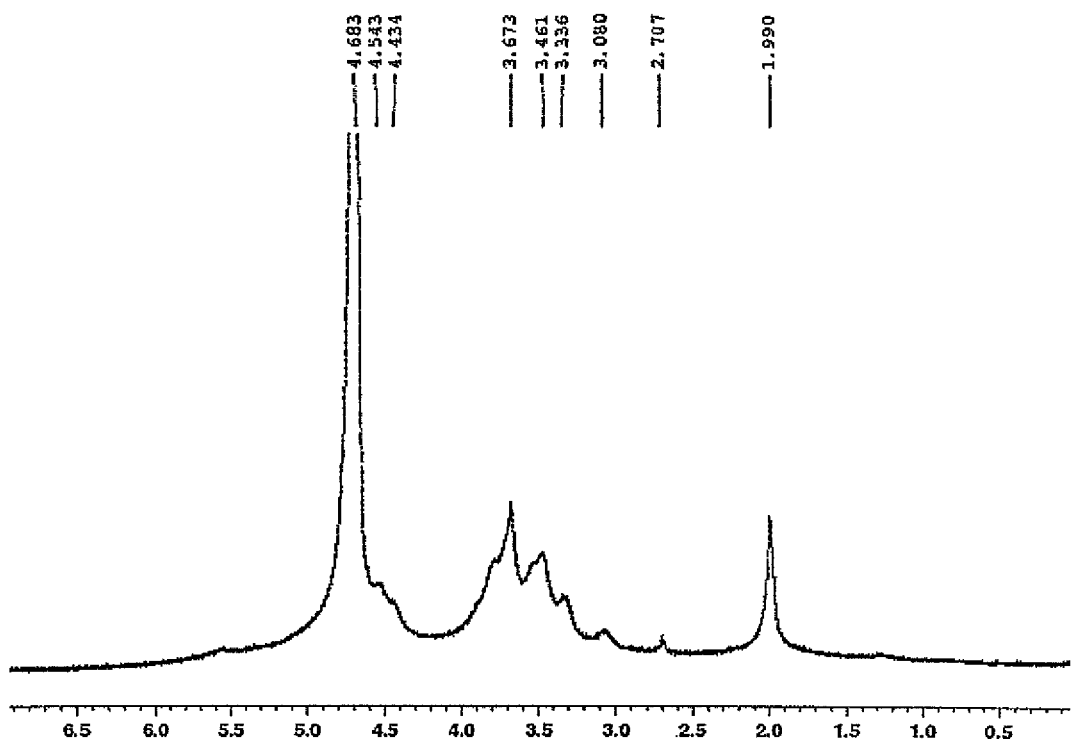
FIG. 1 shows the $^1$H-NMR spectrum ($D_2O$) of HA-EDA derivative having 50% mol/mol of functionalization in ethylenediamine groups, obtained according to the procedure of the invention.

Then it is specific object of this invention a procedure for the production of hyaluronic acid functional derivatives composed of the following subsequent steps:
(a) activation of at least one hydroxyl group of hyaluronic acid (HA) (this HA as salt soluble in organic solvents); reacting this HA salt in polar aprotic solvent with a carbonating agent chosen between carbonic phenylesters or haloformic phenylesters;

(b) reaction of activated HA salt obtained from the step (a), by means of nucleophilic substitution, with a compound having general formula $NH_2$—R, where R can be: $NH_2$, an aminoalkyl group, an alkyl chain, an arylalkyl chain, a polyacrylic chain, a polyoxyethylene chain, or a molecule of low molecilar weight (as example a drug) or a high molecular weight molecule (as example a polymer, a protein, etc); preferably said molecule with low or high molecular weight is biocompatible and soluble either in organic solvents or in aqueous medium.

In particular the carbonating reactive employed for the first step can be the bis(4-nitrophenyl carbonate) (a carbonyl phenyl ester) and/or a chloro nitrophenyl carbonate.

The hyaluronic acid salt soluble in organic solvents should be preferably chosen between the tetrabutylammonic salt (indicated as TBA) or the cetyltrimethylammonium salt (indicated as CTA).

According to some preferred realization aspects of the invention the organic solvent employed for the functionalization reactions is chosen between dimethylsulfoxide, dimethylformamide, dimethyl acetamide and their mixtures and both steps of activation (a) and nucleophilic substitution (b) are carried out at temperatures between 10 and 60° C.

The functionalized degree of the obtained HA derivatives can vary from only one hydroxyl group to the whole hydroxyl groups of HA and it depends (in a manner directly proportional) upon the amount of reactive carbonilating agent used in the above described process. Preferably the functionalization degree varies between 5 and 95%, more preferably between 20 and 80% (for better understanding of this see example 1).

According to other specific embodiments, the compound having general formula $NH_2$—R can be chosen between hydrazine ($NH_2$—$NH_2$) and a bis-amino alkyl group having formula $NH_2$—$(CH_2)_n$—$NH_2$, where n is a number between 1 and 30, preferably between 1 and 10. In another specific embodiment showed in the following experimental section, bifunctional molecules such as ethylenediamine ($NH_2$—$CH_2$—$CH_2$—$NH_2$, named EDA) and hydrazine ($NH_2$—$NH_2$, named Hy) have been linked to the HA backbone to obtain derivatives HA-EDA and HA-Hy respectively.

According to the present invention, a hyaluronic acid derivative such as HA-EDA or HA-Hy can be exploited to produce a hydrogel through an auto crosslinking procedure employing carbodiimides as activating agents or a chemical crosslinking by employing bi-functional crosslinking molecules, such as example glutaraldehyde, or other polyfunctional molecules. Specific details of the mentioned embodiments are in the following experimental part.

The present invention discloses methods to employ organic solvents soluble salts, in particular tetrabutylammonic, of amino or hydrazine hyaluronic acid derivatives or water soluble hyaluronic acid salts obtained using the procedures showed in this invention, to perform further derivatizations. Such derivatizations can be performed in organic solvents or aqueous media. According to other preferred aspects of this invention, a hyaluronic acid salt derivative obtained as in the step (b) of the procedure, follows a further functionalization procedure by a nucleophilic substitution with a molecule having general formula Y—R', where Y is a good leaving group such as a halogen, N-oxysuccinimide, an alkoxyl with 1-6 carbon atoms, or Y is an electrophilic portion of an anhydride or an epoxide, and R' is a portion such as an acryloyl or methacryloyl group both opportunely substituted; a portion of an organic solvent or aqueous solvent soluble molecule.

Preferably, the further functionalization is carried out in polar aprotic solvent chosen between dimethylsulfoxide, dimethylformamide, dimethylacetamide or their mixtures, at temperatures comprised between 5 and 60° C.; following other preferred aspects of the invention, the reaction is carried out in the presence of a catalyst chosen between diethylamine, triethylamine, dimethylaminopyridine and their mixtures.

For the production of acrylic or methacrylic hyaluronic acid derivatives, such compound having formula Y—R' is preferably methacrylic anhydride, methacryloyl chloride, acryloyl chloride, glycidyl acrylate or glycidyl methacrylate; for the production of another particular derivative, showed in the following experimental part, the benzoylcysteine derivative of hyaluronic acid, the compound of general formula Y—R' is the N-oxysuccinimide monoester or diester of the N,N'-dibenzoyl-L-cystine or its similar derivatives.

In this last example, the derivative obtained from this further functionalization is subsequently treated with a reduction procedure to obtain a portion benzoyl-cysteine linked to the hyaluronic acid.

According to a further aspect, the present invention, deals with new products consisting of functionalized derivatives of hyaluronic acid having molecular weight in the range of 50000-1500000 dalton obtainable from process as above described.

Hereinafter there will be presented structural formulae which are to be intended as just representative of the type of functionalization (covalent bonding) which occurs to a HA hydroxyl group when subjected to the above described process. The structures hereinafter reported are not to be intended as representative of the functionalization degree which, as stated above, is instead directly proportional to the amount of reactive carbonilating agent, used in the above process.

According to a preferred embodiment the present invention refers to hyaluronic acid acrylic or methacrylic derivatives having molecular weights comprised between 50000 and 1500000 Daltons obtainable from the process as above described.

The type of functionalization of such methacrylic derivatives could be represented by the following structure describing two consecutive disaccharide units of the starting hyaluronic acid, wherein at least one hydroxy group has been functionalised

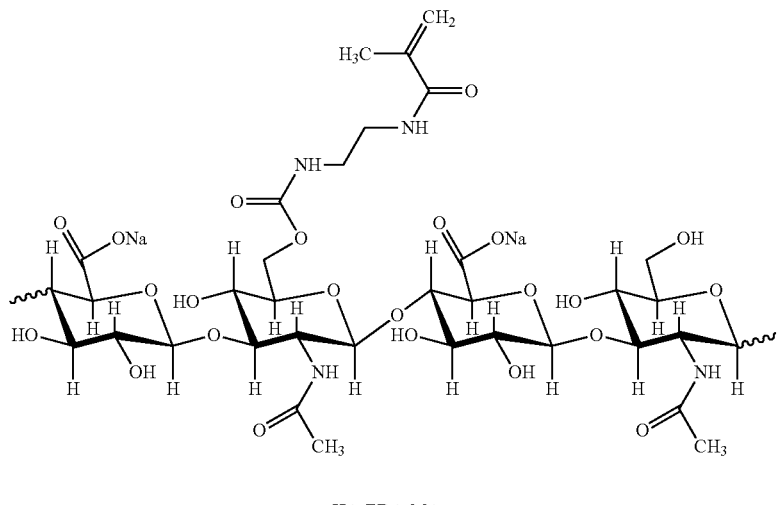

HA-EDA-MA

Acrylic derivatives could be represented by the above formula wherein in place of methacryloyl an acryloyl group is present.

Such acrylic or methacrylic derivatives can be produced according to the "two steps" procedure disclosed by the invention followed from a further functionalization, as above reported.

Moreover it is possible to control the amount of third step functionalization in acrylic or methacrylic groups to obtain derivatives having free amino groups ranging from 5 to 95%.

A crosslinked hydrogel can be obtained from the above described products employing a photocrosslinking procedure, where the concentration of the mentioned functionalized derivative in aqueous or organic solution is comprised between 1% w/v and 20% w/v. Preferably the hydrogel is obtained by irradiating with wavelengths comprised between 180 and 800 nm, with or without radical photoinitiator, with irradiation time comprised between 5 min and 10 hours. Such hydrogels can be obtained also by γ, microwave irradiation or by other ionizing radiations.

Such photocrosslinking can occurs also in the presence of appropriate additives as acrylic and methacrylic monomers, polyethylenglycole methacrylates and acrylates, both mono and polyfunctional, or in the presence of other additives employed to change or improve plasticity, hardness, hydrophilic and lipophilic character.

According to a further aspect of the invention, this has as specific objective a new derivative obtained according to the proposed two steps procedure, the hyaluronic acid benzoylcysteine derivative or its similar derivatives having molecular weight comprised between 50000 and 1500000 Daltons, obtainable from the above described process. Such hyaluronic acid benzoylcysteine derivatives could be represented by the following structure, referred to two consecutive disaccharides units of the starting hyaluronic acid, wherein at least one hydroxy group has been functionalised:

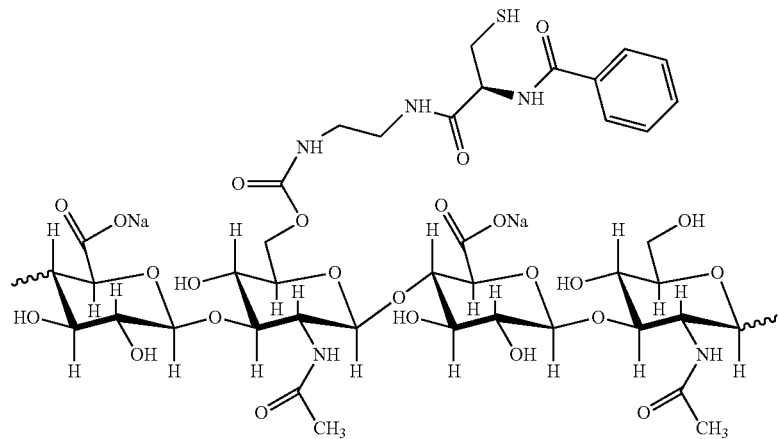

HA-EDA-BC

Such aminoacidic derivative can be obtained following the two steps procedure according to the invention, and then following a further functionalization, as above described and by a subsequent hyaluronic acid derivative disulfide bridge reduction.

In this case it is possible to obtain a crosslinked hydrogel even by oxidation to the air.

In general, the present invention includes in its scope hydrogels obtained by means of the described methods, such hydrogels can be produced, applying the appropriate technical procedures, as nanoparticles or microparticles, films, membrane, fibers and scaffolds.

Finally this invention concerns the use of the described hydrogels for the production of drug or gene delivery devices, for cosmetic and agroalimentary uses, for the production of wounds, organs or tissues covering systems, of implantable materials and scaffolds for the tissue regeneration.

The specific characteristics of this invention, as its advantages and its methodologies and specific applications examples referred to further functionalizations of the derivatives, and hydrogels preparation, will be clearer into the detailed exemplificative description in the following.

EXPERIMENTAL PART

Example 1

Synthesis of Hyaluronic Acid-Ethylenediamine Derivative (HA-EDA)

3 g of tetrabutylammonium salt of hyaluronic acid (HA-TBA) prepared by hyaluronic acid solution neutralization using tetrabutylammonium hydroxide solution, were dissolved in 270 ml of anhydrous dimethylsulfoxide (weight-average molecular weight of hyaluronic acid 270 kDa).

The suitable amount of bis(4-nithrophenyl) carbonate (4-NPBC) chosen in a way to obtain ratios moles of 4-NPBC/moles of HA-TBA respectively equal to 0.75, 0.5 and 0.25 were dissolved in 30 ml of anhydrous dimethylsulfoxide; this solution was added drop by drop to the HA-TBA solution at 40° C. under stirring. After 4 h, 3 ml of ethylendiamine (EDA) were added drop by drop and the solution was left at 40° C. for other 3 h. Then the work-up of the reaction was accomplished by first precipitating the hyaluronic acid derivative into acetone then washing in the same solvent until a product without reaction intermediates has been obtained.

The obtained solid, formed by HA-TBA-EDA copolymer, was finely pounded.

The sodium salt of the ethylendiamino derivative of HA, the derivative HA-EDA, has been obtained fluxing the solution in dimethylsulfoxide of HA-TBA-EDA through a column loaded with DOWEX 50 Wx8 resin activated in its sodium form. The product was recovered exchanging the DMSO solution against water using a dialysis procedure and then freeze-drying the aqueous solution.

Scheme 1 shows the procedure of functionalization.

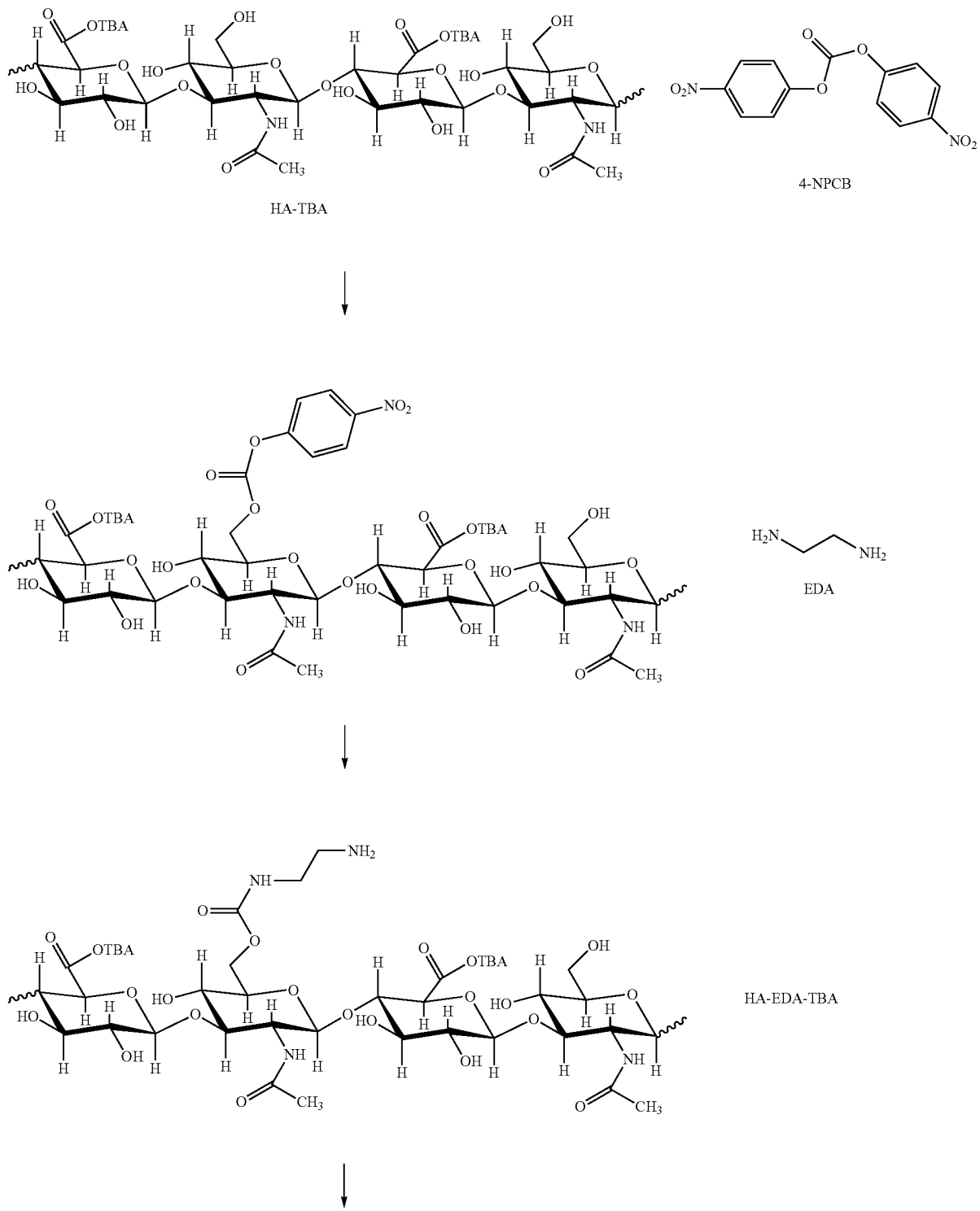

Scheme 1 - Reaction of functionalization of tetrabutylammonium salt of hyaluronic acid (HA-TBA) with ethylenediamine, to obtain HA-EDA derivative

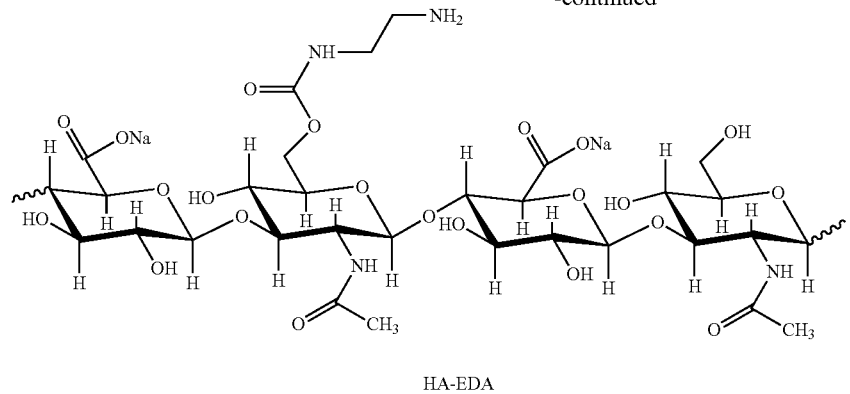

HA-EDA

The HA-EDA derivative was characterized by $^1$H-NMR analysis as showed in the spectrum reported in FIG. 1 (see drawings). In particular $^1$H-NMR ($D_2O$) showed: δ 1.9 (m, —NH—CO—$CH_3$); δ 3.1 (m, CO—NH—$CH_2$—$CH_2$—$NH_2$).

Functionalization degree has been calculated by comparing the area of the peak at δ 1.9 attributable to the $CH_3$ of the N-acetylglucosamine portion of HA with the area of the peak at δ 3.1 attributable to the ethylenediamine portion linked to the HA. The functionalization degree has been expressed as % moles of ethylenediamine portion inserted per moles of repetitive unit of HA.

The following Table 1 shows as example the molar functionalization in ethylenediamine groups linked to the HA obtained employing three different ratios moles 4-NPBC/moles HA-TBA repetitive units

TABLE 1

| Moles 4-NPBC/moles HA-TBA repetitive units | Molar functionalization degree in ethylenediamine groups linked to hyaluronic acid |
|---|---|
| 0.25 | 22% mol/mol |
| 0.50 | 52% mol/mol |
| 0.75 | 70% mol/mol |

Example 2

Synthesis of Hyaluronic Acid-Hydrazine Derivative (HA-Hy)

3 g of tetrabutylammonium salt of hyaluronic acid (HA-TBA) were dissolved in 270 ml of anhydrous dimethylsulfoxide (weight-average molecular weight of hyaluronic acid 270 kDa). 30 ml of an anhydrous dimethylsulfoxide solution containing 0.73 g of bis(4-nithrophenyl)carbonate (4-NPBC) were added drop by drop to the HA-TBA solution and left to react for 4 h at 40° C. under stirring. After this time 2.7 ml of hydrazine monohydrate were added drop by drop and the solution was left at 40° C. for other 1 h. Then the work-up of the reaction was accomplished by first precipitating the hyaluronic acid derivative in diethyl ether then by washing with acetone. To obtain the sodium salt of the HA-Hy the reaction solution was fluxed through a column loaded with DOWEX 50 Wx8 resin activated in its sodium form then precipitated in acetone and washed with the same solvent. Then, the obtained solid was dissolved in water, dialyzed against water then freeze-dried. The functionalization degree, detected by colorimetric assay using trinitrobenzenesulfonic acid (TNSB) was equal to 50% mol/mol.

Scheme 2 shows the reaction procedure.

Scheme 2 - Reaction of functionalization of tetrabutylammonium salt of hyaluronic acid (HA-TBA) with hydrazine monohydrate to obtain HA-Hy derivative

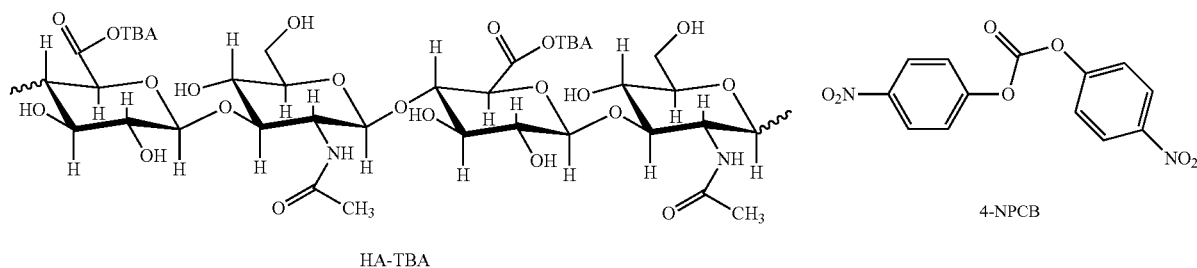

HA-TBA

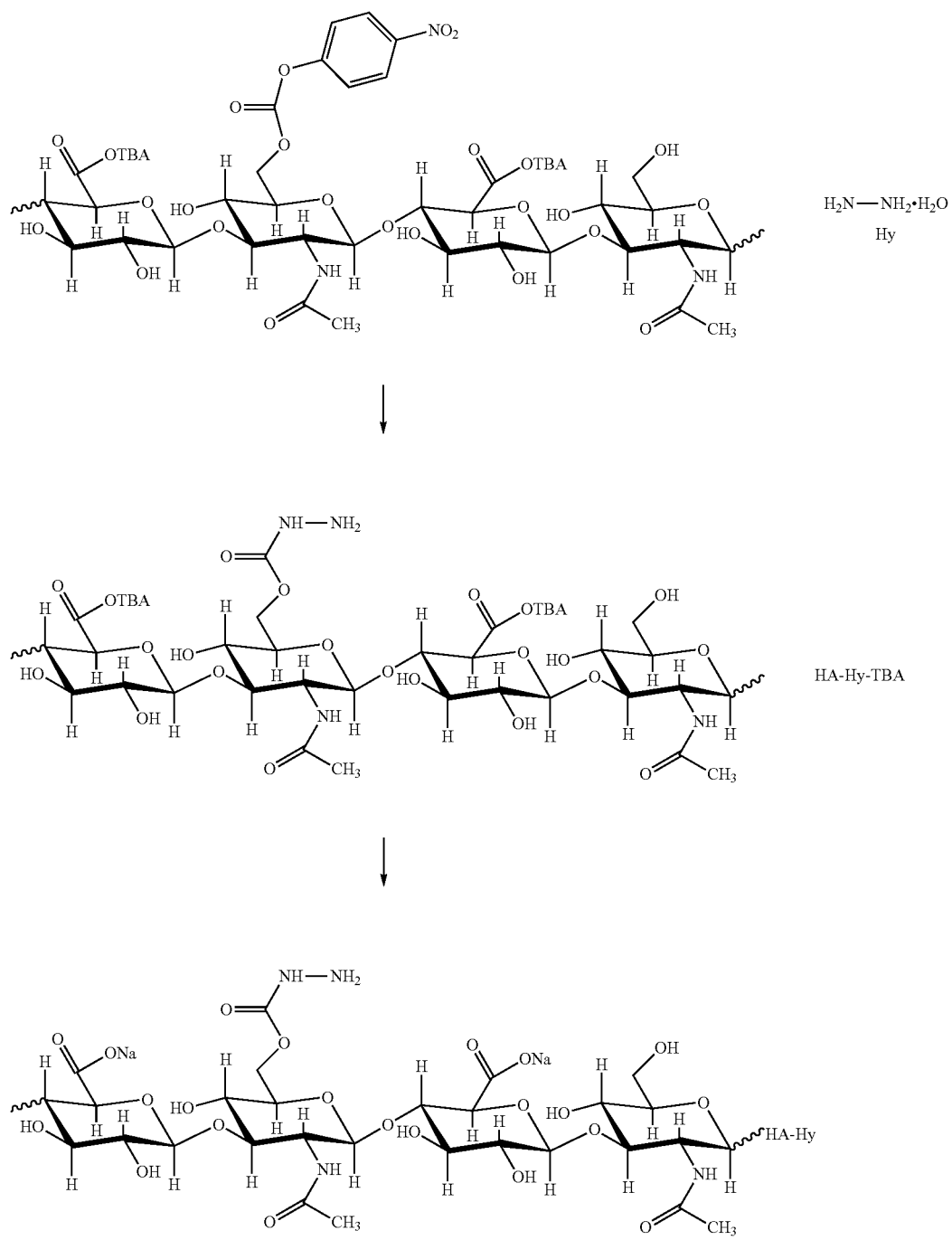

Example 3

Synthesis of the Hyaluronic Acid Derivative Functionalized with Butylamine (HA-BTA)

3 g of tetrabutylammonium salt of hyaluronic acid (HA-TBA) were dissolved in 270 ml of anhydrous dimethylsulfoxide (weight-average molecular weight of hyaluronic acid 270 kDa). 30 ml of an anhydrous dimethylsulfoxide solution containing 0.73 g of bis(4-nithrophenyl) carbonate (4-NPBC) were added drop by drop to the HA-TBA solution and left to react for 4 h at 40° C. under stirring. After this time 4.7 ml of butylamine were added drop by drop and the reaction mixture was left at 40° C. for 24 h. Then, the reaction solution was fluxed through a column loaded with DOWEX 50 Wx8 resin activated in its sodium form then precipitated in acetone and washed with the same solvent, finally dialyzed against water and freeze-dried. On the obtained derivative, named HA-BTA, the absence of unreacted butylamine was confirmed by trinitrobenzenesulfonic acid assay (TNSB).
The scheme 3 shows the functionalization procedure.
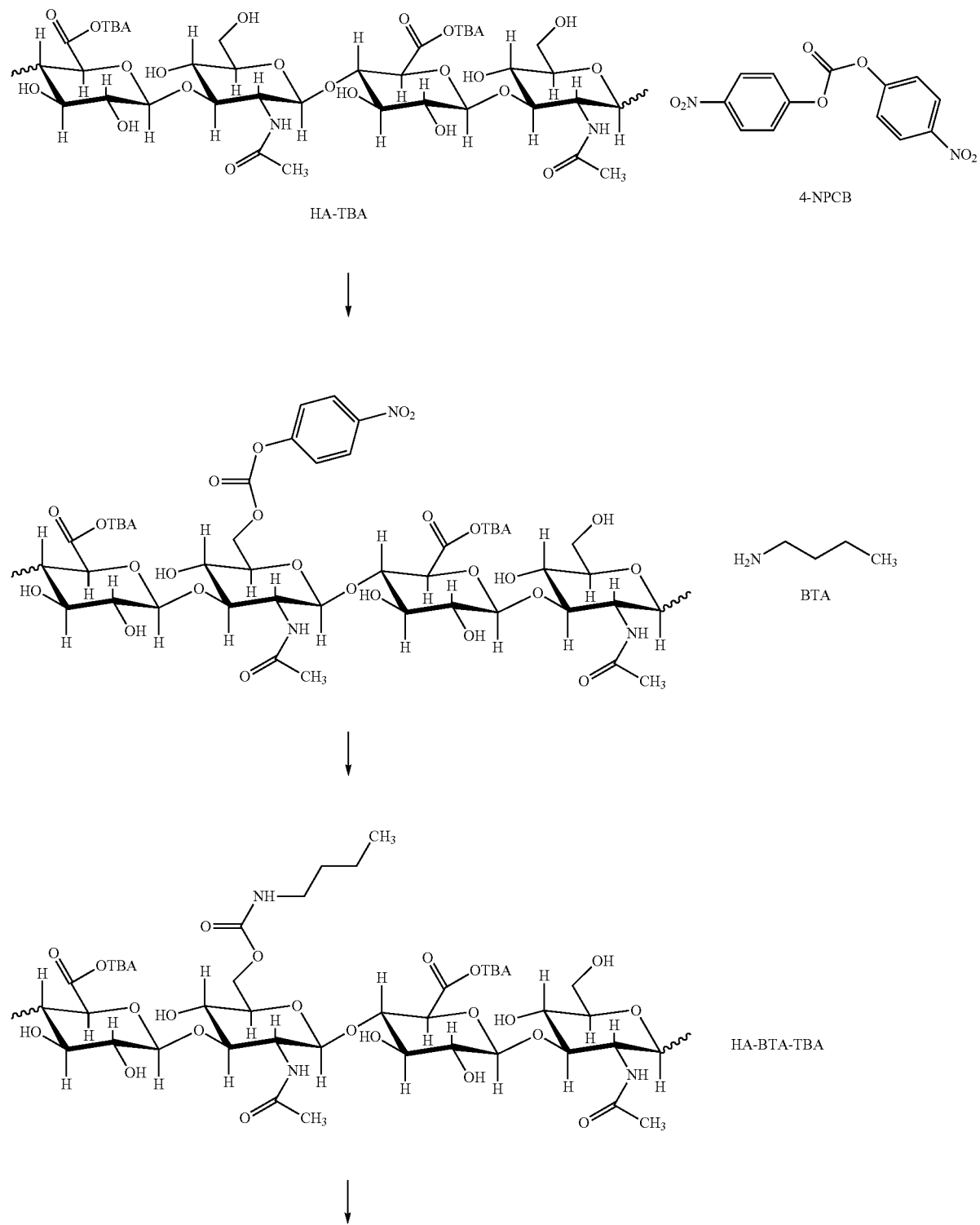
Scheme 3 - Reaction of functionalization of tetrabutylammonium salt of hyaluronic acid (HA-TBA) with butylamine (BTA), to obtain HA-BTA derivative

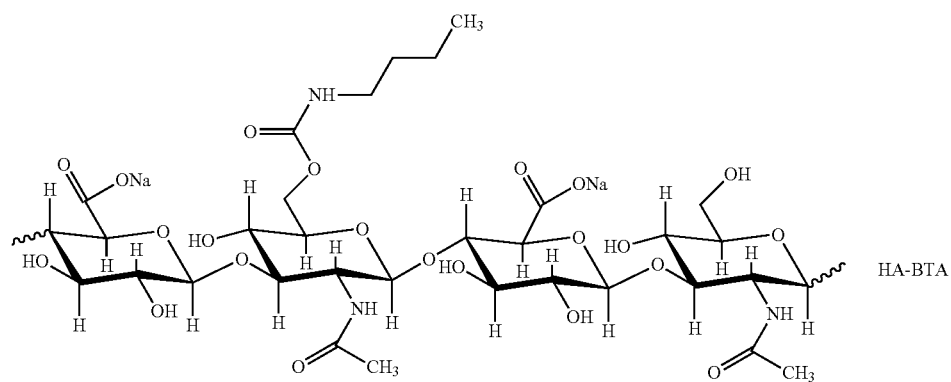

HA-BTA

Figure 2:
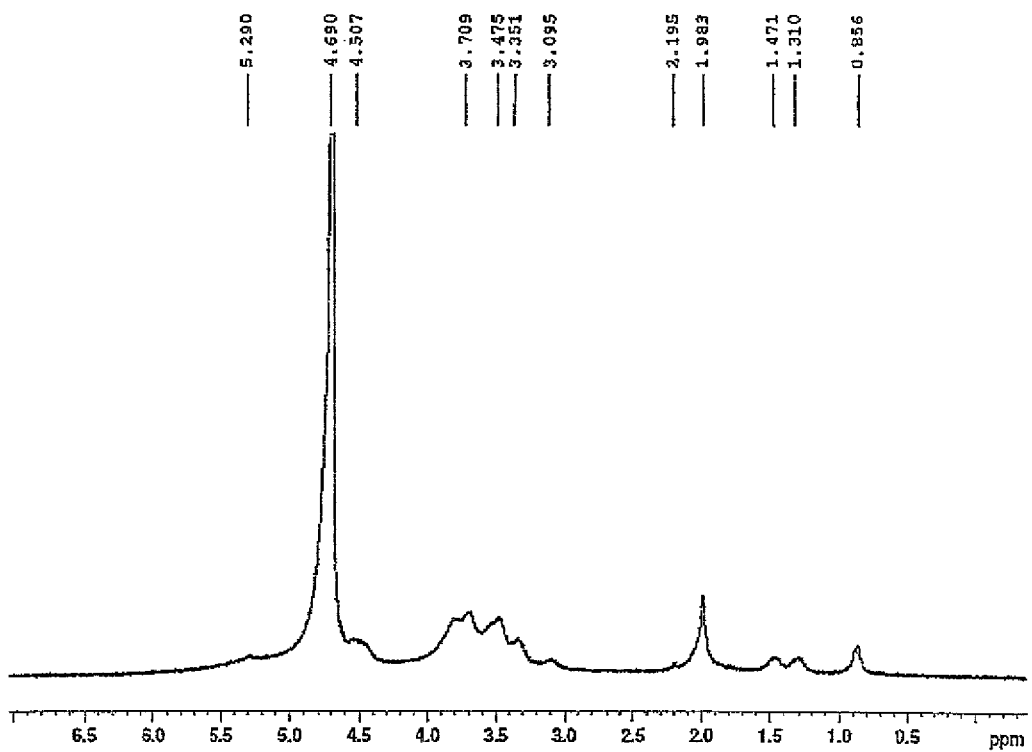
FIG. 2 shows the $^1$H-NMR spectrum ($D_2O$) of HA-BTA derivative having 52% mol/mol of functionalization in butyl groups obtained according to the procedure of the invention.

The derivative HA-BTA was characterized by $^1$H-NMR as showed in FIG. 2 of drawings, showing the following signals (D$_2$O): δ 0.8 (—NH—CH$_2$—CH$_2$—CH$_2$—CH$_3$); δ 1.3 (—NHCH$_2$—CH$_2$—CH$_2$—CH$_3$); δ 1.4 (—NH—CH$_2$—CH$_2$—CH$_2$—CH$_3$); δ 2.0 (s, —NH—COCH$_3$); δ 3.1 (—NH—CH$_2$—CH$_2$—CH$_2$—CH$_3$). The functionalization degree has been calculated by comparing the areas of peaks at δ 0.8, 1.3, 1.4 and 3.1 attributable to the methylene of the butylamine chain with the area of the peak at δ 2.0 attributable to the methyl group of the N-acetylglucosamine portion of HA. The functionalization degree was equal to 52% mol/mol.

Example 4

Synthesis of Hyaluronic Acid-Aminopolyethylene Glycol Derivative (HA-NH-PEG)

1 g of tetrabutylammonium salt of HA (HA-TBA) (weight-average molecular weight of starting hyaluronic acid equal to 230 kDa) was dissolved in 90 ml of anhydrous dimethylsulfoxide. 0.4 g of bis(4-nithrophenyl) carbonate (4-NPBC) were dissolved in 10 ml of anhydrous dimethylsulfoxide. The solution of 4-NPBC was added drop by drop to the HA-TBA solution at 40° C. under stirring, then the reaction was left at the same temperature for 4 h.

After this time, 6 g of O-(2-aminoethyl)-O-methyl-polyethylene glycol (PEG-NH$_2$) (molecular weight 750 Da) dissolved in 5 ml of dimethylsulfoxide were added drop by drop and the solution was left at 40° C. for 24 h. Then, the reaction solution was fluxed through a column loaded with DOWEX 50 Wx8 resin activated in its sodium form then precipitated in acetone and washed with the same solvent. The obtained product, named HA-NH-PEG, after freeze-drying was dissolved in water and dialyzed against water for 5 days by using a dialysis membrane Spectrapor having a molecular cut-off equal to 12000-14000.

The following scheme 4 shows the procedure of functionalization.

Scheme 4 - Reaction of functionalization of tetrabutylammonium salt of hyaluronic acid (HA-TBA) with O-(2-aminoethyl)-O-methyl-polyethylene glycol (PEG-NH$_2$) to obtain the derivative HA-NH-PEG

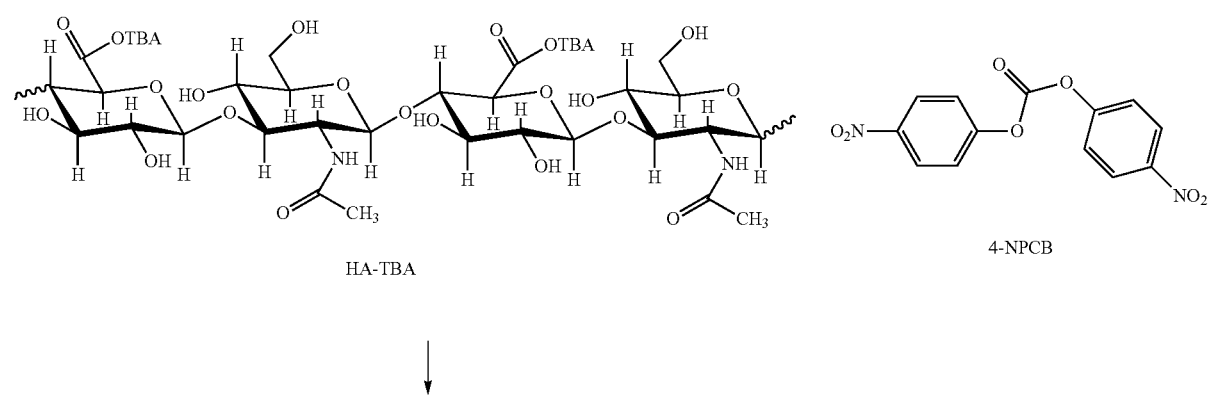

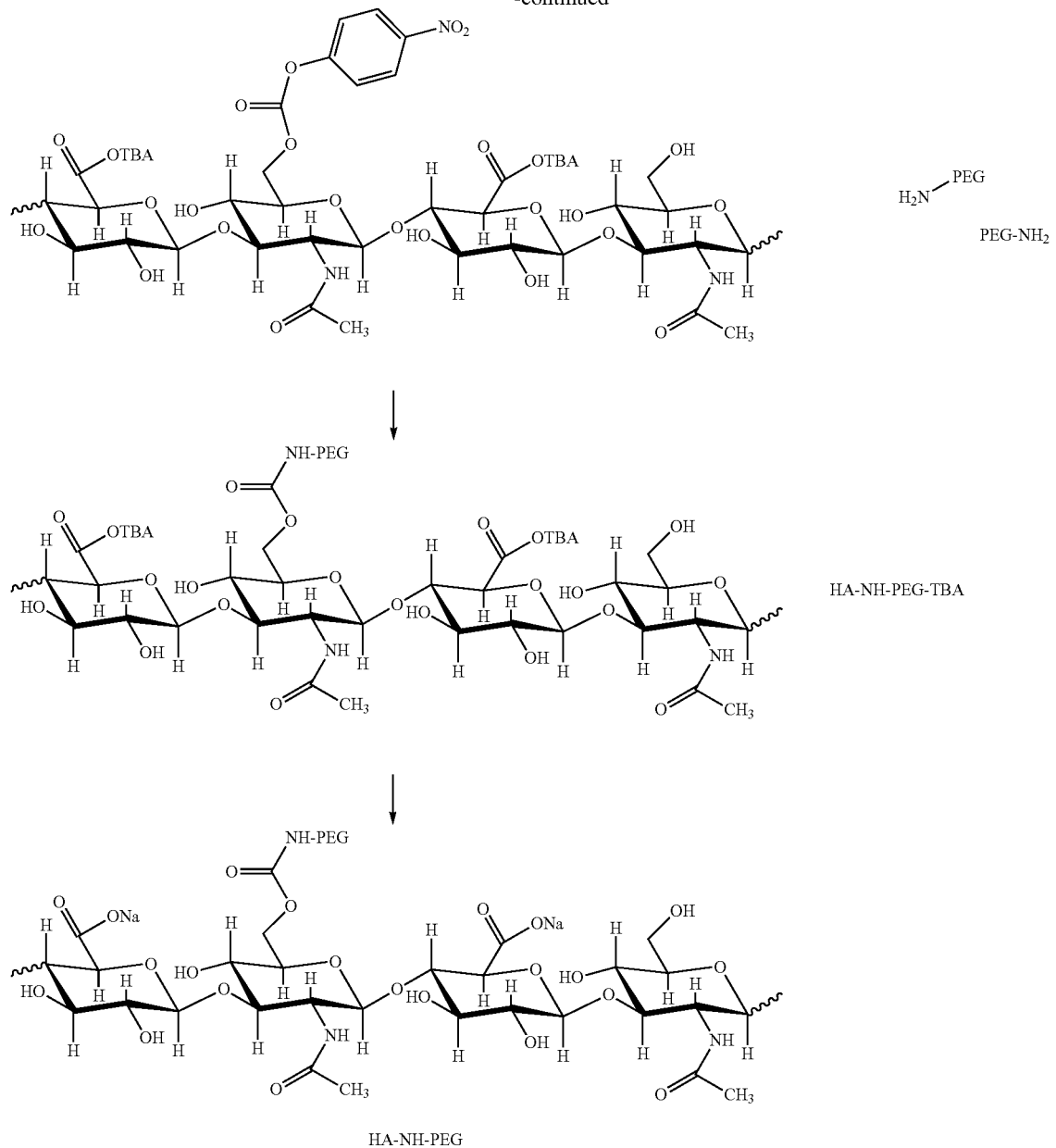

HA-NH-PEG

The absence of unreacted PEG-NH$_2$ was confirmed by NTSB colorimetric assay for free amino groups.

Figure 3:
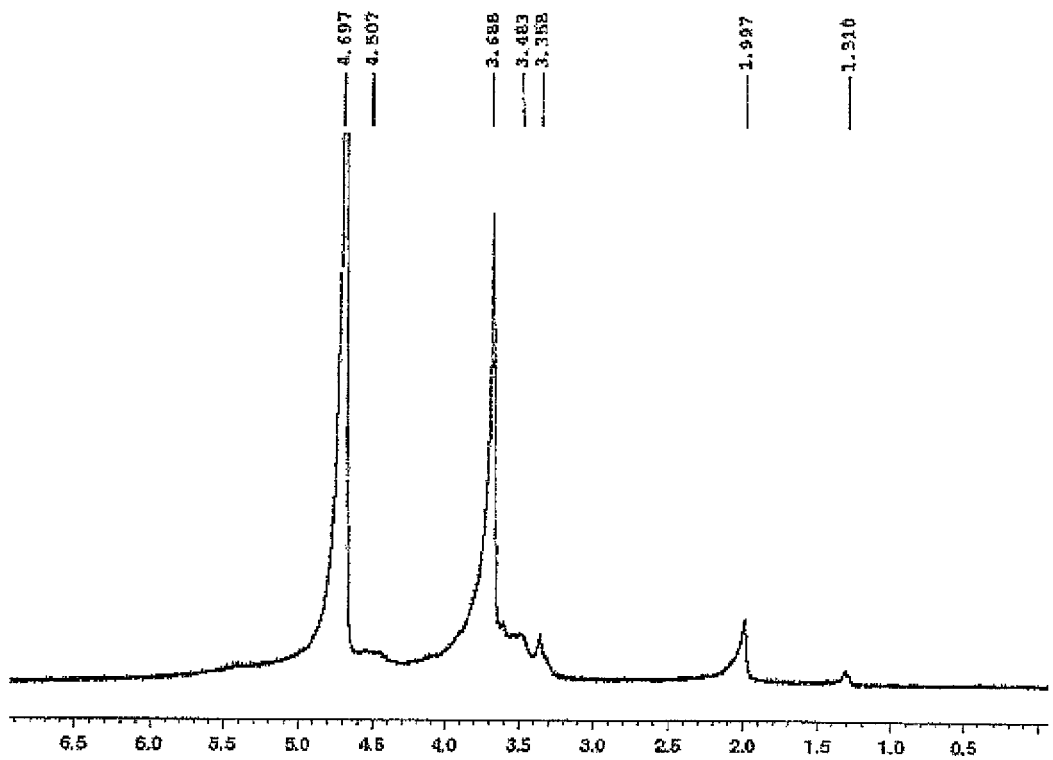
FIG. 3 shows the $^1$H-NMR spectrum ($D_2O$) of the HA-NH-PEG derivative, having 33% mol/mol of functionalization in polyoxyethylene-monomethyl-monoamino chains obtained according to the procedure of the invention.

The derivative HA-NH-PEG has been characterized by $^1$H-NMR as showed in FIG. 3 of the attached drawings, where the following peaks are present (D$_2$O): δ 1.4 (s, —CO—NH—(O—CH$_2$—CH$_2$)n-O—CH$_3$) δ 2.0 (s, —NH—CO—CH$_3$); δ 3.7 (s, —CO—NH—(O—CH$_2$—CH$_2$)n-O—CH$_3$). The functionalization degree was equal to 33% mol/mol.

Preparation of Methacrylic Derivatives of Hyaluronic Acid-Ethylendiamine (HA-EDA-MA)

Considering the interest to produce photocrosslinkable hyaluronic acid derivatives affordable in tissue engineering, in drug delivery field, tissue augmentation etc, one of the more advantageous application of the method here proposed, is the functionalization of hyaluronic acid amino copolymers with methacrylic portions.

In scientific literature several examples of methacrylic hyaluronic acid derivatives have been reported. In the procedure firstly described by de Smeds et al. (J. Biomed. Mat. Res. 2001; 54(1):115-121) the HA-methacrylic derivative (HA-MA) was produced in aqueous environment by using a 20-fold molar excess of methacrylic anhydride relative to primary hydroxyl groups of HA. Nevertheless, using this procedure a two phases system is formed thus reducing the functionalization efficiency.

Recently Oudshoorn et al. (Polymer 48 (2007) 1915-1920) described the formation of HA-MA copolymer by employing a reaction in organic polar aprotic solvent (dimethylsulfoxide) between tetrabutylammonium salt of HA and glycidyl methacrylate (GMA). In this case only a 30% mol/mol of functionalization was obtained by using a ratio moles GMA moles hydroxyl groups of HA equal to 200.

In the method here disclosed the presence of the more nucleophilic group in the hyaluronic acid side chain (as example the amino group of the ethylenediamine derivative of hyaluronic acid) could be conveniently exploited to obtain a more efficient functionalization employing as example methacrylic-anhydride (AMA) as reactant.

In order to study the potentiality of the method and to demonstrate the selective functionalization of the free amino groups on the HA, three different batches of tetrabutylammonium salt of hyaluronic acid amino derivatives (HA-TBA-EDA) having a molar functionalization degree equal to 75, 50 and 25% mol/mol (as obtained from example 1) respectively, have been prepared by employing the procedure described in the following Example 5. In particular in this example, just a two fold molar excess of AMA compared to the HA-TBA-EDA free amino groups was enough to obtain the complete functionalization of all amino groups present on HA-ethylenediamine derivative, obtaining the copolymers named HA-EDA-MA. The absence of unreacted amino groups in HA-EDA-MA copolymers was evaluated by colorimetric assay employing trinitrobenzenesulfonic acid (TNBS). Moreover it is possible to control the amount of functionalization in methacrylic groups to obtain HA-EDA-MA derivatives having free amino groups ranging from 5 to 95%.

Example 5

Synthesis of Hyaluronic Acid-Ethylendiamine Methacrylic Derivatives (HA-EDA-MA)

1 g of HA-TBA-EDA obtained as reported in the Example 1 having a functionalization degree in ethylendiamine groups equal to 50% mol/mol, was dissolved in 100 ml of anhydrous dimethylsulfoxide (DMSO). Then an appropriate volume of methacrylic anhydride (AMA) to obtain a two fold molar excess compared to the moles of amino groups on to the HA-TBA-EDA, was added. The catalyst diethylamine was added in equimolar ratio to the moles of amino groups of HA-EDA-TBA, and the final solution was left for 24 h at 40° C.

After this time the organic solution was fluxed in a column containing sodium activated DOWEX 50 W×8 resin. The eluted solution was then precipitated in acetone and the obtained solid, named HA-EDA-MA was washed several times with the same solvent then dried, dissolved in water and dialyzed against distilled water. The solution was filtered then freeze dried. Scheme 5 shows the reaction procedure.

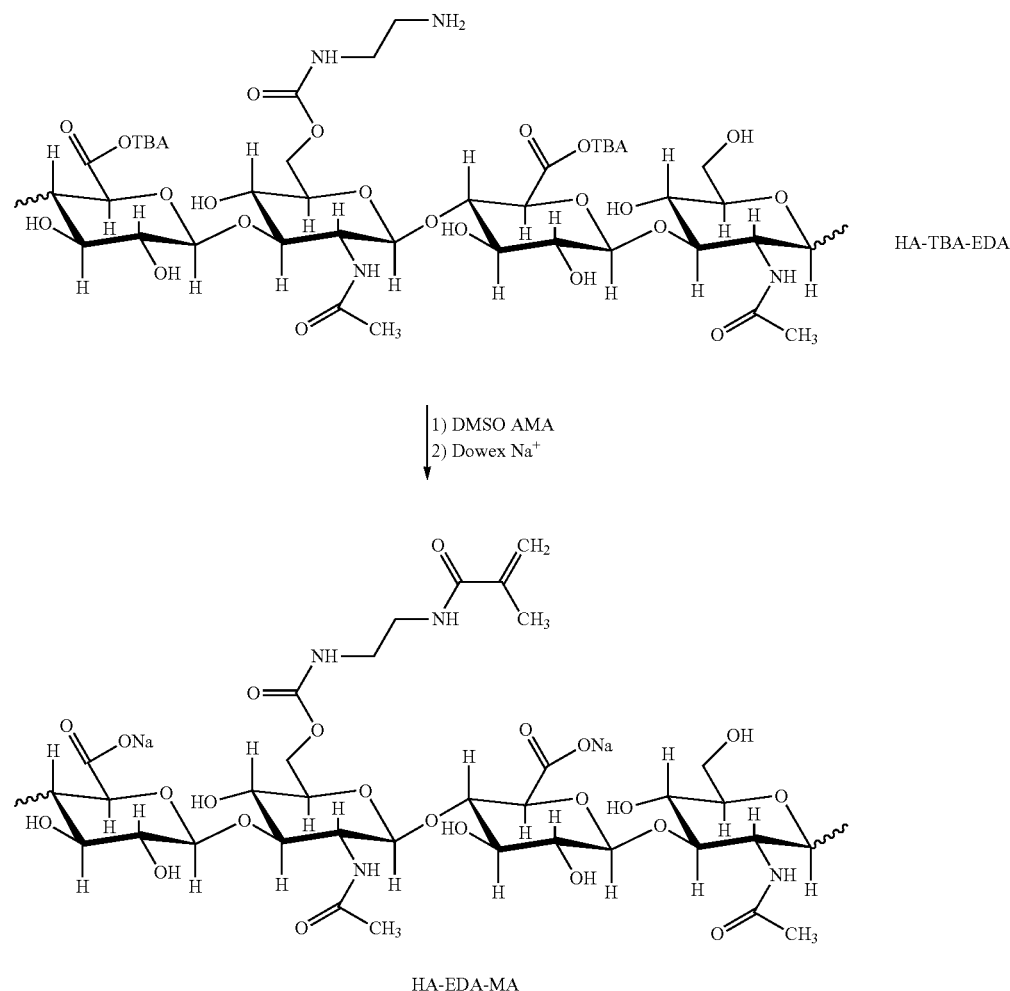

Figure 4:
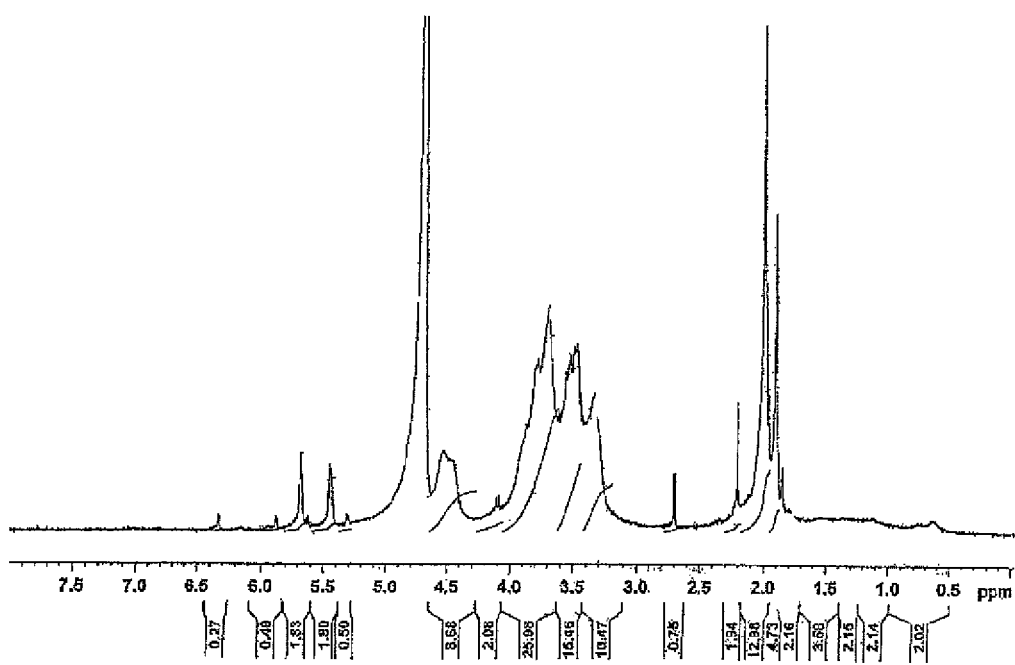
FIG. 4 shows the $^1$H-NMR spectrum ($D_2O$) of HA-EDA-MA derivative having 50% mol/mol of functionalization in ethylendiamine groups and 50% mol/mol of functionalization in methacrylic groups, obtained according to the procedure of the invention.

Scheme 5 - Reaction of functionalization of hyaluronic acid-ethylenediamine tetrabutylammonium salt (HA-EDA-TBA) with methacrylic anhydride (AMA) to obtain HA-EDA-MA derivative The HA-EDA-MA derivative was characterized by ¹H-NMR (see FIG. 4), showing the following peaks (D₂O): δ 1.9 (s, —CO—CH═CH—CH₃); δ 2.0 (s, —NH—CO—CH₃); δ 5.5 e 5.8 (m, —CO—CH═CH—CH₃).

The functionalization degree has been evaluated by comparing the areas of peaks at δ 5.5 and 5.8 attributable to the vinyl protons of the methacrylic group with the area at δ 1.9 attributable to the methyl group of the N-acetylglucosamine portion of HA repetitive units. The functionalization degree in methacrylic groups linked to repetitive units of HA-EDA resulted equal to 50% mol/mol, i.e. all amino groups have been derivatized with methacrylic anhydride Preparation of Hyaluronic Acid-Ethylenediamine-Benzoylcysteine Derivative (HA-EDA-BC)

One of the most important structural properties of the extracellular matrix, is its fibrillar structure due to the presence of collagen and other proteins. This fibrillar structure is fundamental for the connection of the cells with the environment and for the optimal diffusion of humoral factors and nutrients. Recently, many efforts are addressed to the possibility to produce artificial scaffolds with a fibrillar structure (*Biomaterials* 29 (2008) 1989-2006).

In this context, a possibility concerns the production of hybrid copolymers able to spontaneously assemble with a precise hierarchical structure. For example Zhang et al. produced self complementary oligopeptides able to spontaneously form fibrillar scaffolds when dissolved in aqueous buffers; these matrices have found various applications in tissue engineering field (*Chemical Biology* 2002, 6:865-871).

The interest to produce scaffolds able to autocross-link after injection into the body is justified by the fact that their direct deposition on the organ or tissue injury (i.e. for the reconstruction of the articular cartilage) can avoid the necessity of a surgical implantation, then facilitating the integration of the new formed extracellular matrix with the host tissue.

From this point of view it is fundamental that the crosslinking should not involve reactions potentially toxic for the tissues, moreover the reaction should allow the encapsulation of the matrix regenerating cells without interfering with their viability (*Advanced Drug Delivery Reviews* 59 (2007) 263-273). For example Shu et al. has recently developed a thiol hyaluronic acid derivative able to slowly crosslink by air oxidation or fastly to crosslink if PEG-diacrylate derivatives are employed as crosslinking agents (*Biomaterials* 25 (2004) 1339-1348; Biomaterials 24 (2003) 3825-3834 WO 2005/056608).

Some non polymeric compounds are able to spontaneously assemble both in organic and aqueous media to form hydrogels. For example the aminoacid N—N' dibenzoyl-L-cystine (DBC) and its derivatives (*J. Med. Chem.* 1967, 10,1172) forms hydrogels by spontaneous self assembling even at very low concentration. The driving force of this spontaneous aggregation is the formation of π-π stacking interactions promoted by the aryl groups (*Angew. Chem. Int. Ed. Engl.* 1995, 34, 584; *J. Am. Chem. Soc* 2000, 122, 11679-11691).

Considering the properties of DBC and its derivatives to produce fibrillar hydrogels by spontaneous self assembling and since the presence of a disulfide bridge could be, in case of need, reversibly broken, by a simple oxide-reductive reaction, to form free thiol groups, then again oxidized to form a S—S bridge, the method reported in the present invention, can be employed to synthesize the derivative hyaluronic acid-ethylendiamine-benzoylcysteine (HA-EDA-BC) able to exploit both oxidative and self assembling properties to produce a fibrillar structure.

Example 6

Synthesis of Hyaluronic Acid-Ethylenediamine-Benzoylcysteine Derivative (HA-EDA-BC)

1.3 g of N,N'-dibenzoyl-L-cistyne (DBC) are dissolved in 28 ml of dichloromethane and 20 ml of anhydrous dimethylsulfoxide. 0.6 g of dicyclohexylcarbodiimide (DCC) and 0.34 g of N-hydroxysuccinimide (NHS) have been added to this solution. The activation reaction has been performed at room temperature for 24 h. After this time the solution has been filtered and the excess of dichloromethane has been removed under vacuum.

This solution containing the N-oxysuccinimide derivative of N,N'-dibenzoyl-L-cistyne (DBC-NOS) has been added drop by drop to 80 ml of dimethylsulfoxide containing 1 g of HA-TBA-EDA with a functionalization degree of 30% mol/mol in amino groups. The reaction has been carried out with diethylamine as a catalyst (960 d).

After 28 hours at 40° C. the solution has been eluted in a column loaded with resin DOWEX 50 W×8 activated in its sodium form, then the copolymer has been precipitated in diethyl ether, and washed with ethanol and acetone. The HA-EDA-DBC thus obtained has been finely pounded and then dispersed in water until a homogeneous hydrogel has been obtained. Then the pH of the obtained hydrogel has been adjusted to 8 adding NaOH 1N and then 1.2 g of dithiothreitol have been added to reduce the disulfide bridge obtaining the derivative hyaluronic acid-ethylenediamine-benzoylcysteine (HA-EDA-BC).

The solution has been left for 24 h at room temperature and, after regulating the pH to 3.5, it has been dialyzed against acidic water for 5 days. Then the solution has been filtered, and freeze-dried. The following Scheme 6 shows the functionalization procedure described above.

Scheme 6 - Reaction of functionalization reaction of hyaluronic acid-ethylenediamine tetrabutylammonium salt (HA-TBA-EDA) with the N-oxysuccinimide derivative of N,N'-dibenzoyl-L-cystine (DBC-NOS), and subsequent disulfide bridge reduction to obtain the derivative hyaluronic acid-ethylenediamine-benzoylcysteine (HA-EDA-BC).

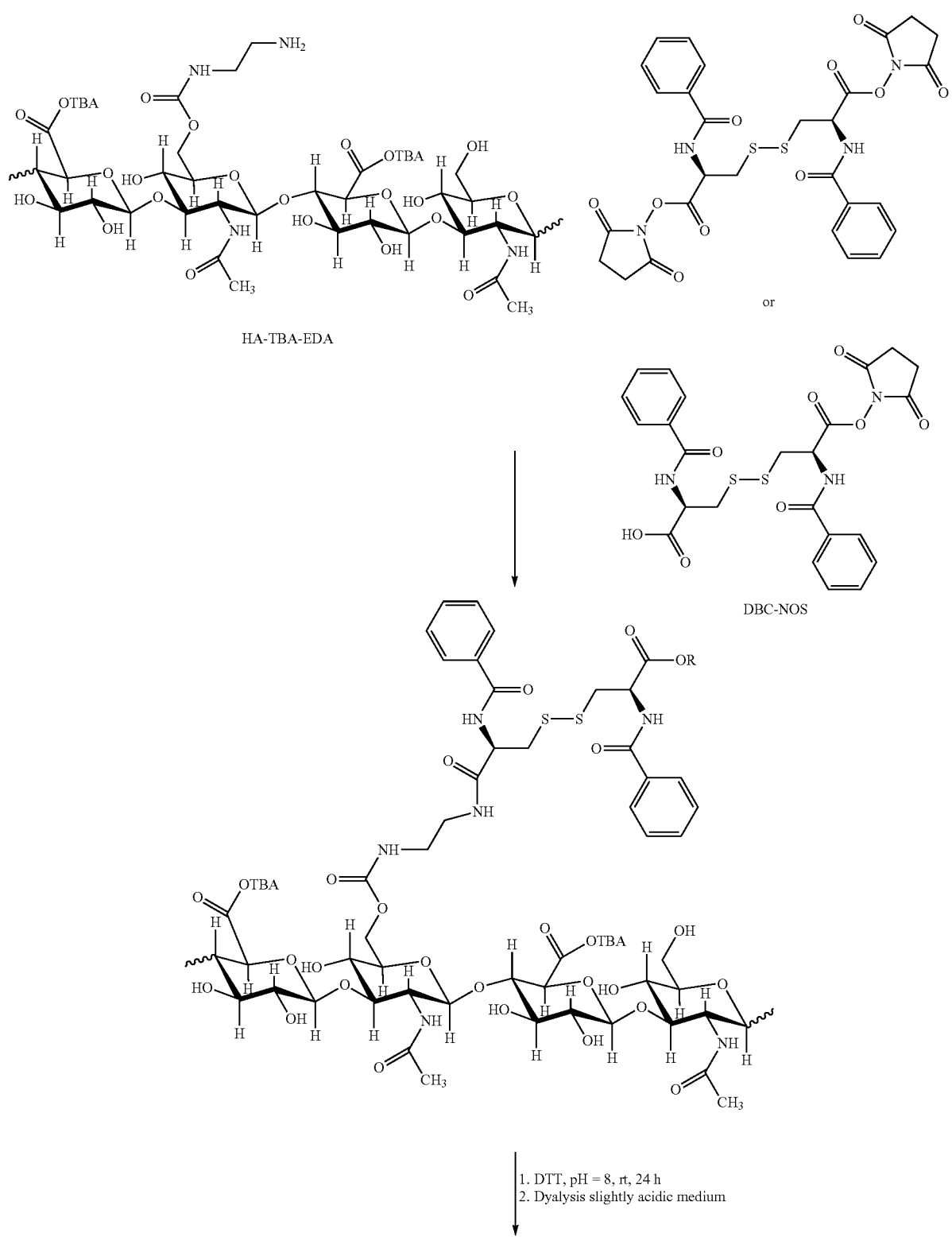

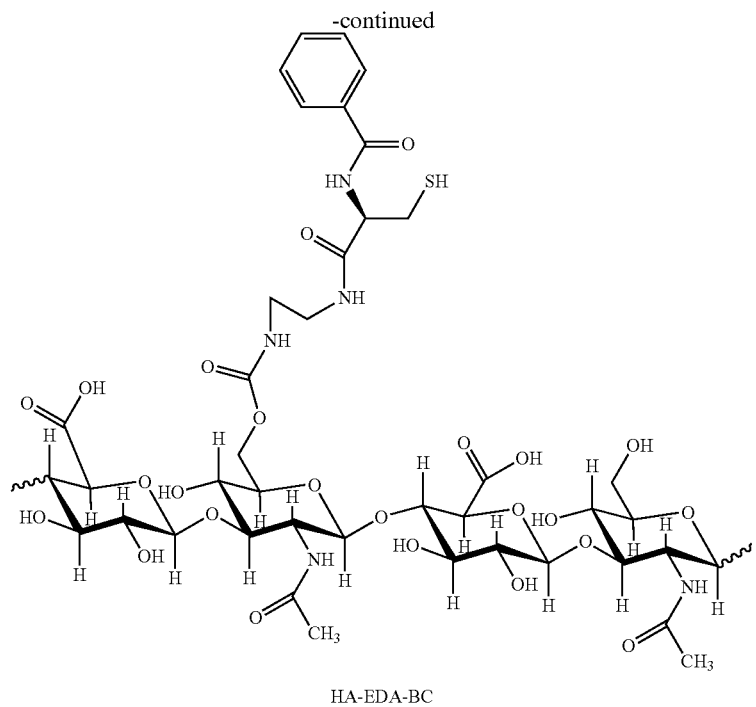

HA-EDA-BC $^1$H-NMR and colorimetric analyses showed a functionalization degree of HA with benzoylcysteine equal to 30% mol/mol. The colorimetric analysis with TNSB demonstrated the absence of amino groups unreacted in HA-EDA-BC derivative.

Crosslinked Hyaluronic Acid Derivatives Hydrogels

The crosslinking of methacrylic hyaluronic acid derivatives of the series HA-EDA-MA was carried out in aqueous or organic medium with or without photoinitiators after irradiation with γ rays, UV rays, visible irradiation, microwaves. It has been experimentally confirmed that aqueous solutions (in the range of concentration 1-20% w/v) of HA-EDA-MA copolymers having various molar functionalization degrees in ethylenediamine or methacrylic groups linked to hyaluronic acid, obtained according to the procedures of this invention, produce hydrogels after exposition to radiations having wavelengths comprised between 180 and 800 nm, or employing a microwave source, as employing a γ rays source or other ionizing sources.

Crosslinking of the HA-hydrazine derivative (HA-Hy) was performed in aqueous environment preferably at pH 4.75 in the presence of water soluble carbodiimides, for example (1-ethyl-3-(3-dimethylaminopropyl)carbodiimide) (EDCI).

The crosslinking of the ethylenediamine hyaluronic acid derivative (HA-EDA) was carried out in phosphate buffer pH 7-8 by employing bifunctional or polyfunctional crosslinking agents, preferably the glutaraldehyde.

The crosslinking of the HA-EDA-BC derivative was carried out in phosphate buffer preferably at pH 7.4 by air oxidation process.

Example 7

Production of HA-EDA-MA Based Hydrogels

Aqueous solutions of HA-EDA-MA copolymer obtained following the Example 5, with a molar functionalization degree equal to 50% mol/mol in ethylenediamine groups and 50% mol/mol in methacrylic groups linked to the HA, and with a concentration ranging from 1 and 20% w/v, were stratified in a Petri dish thus obtaining a thickness of few millimeters.

The Petri dishes were allocated in a refrigerate box at 12° C., and irradiated employing a Polymer (Italquartz, Milan) lamp of 125 Watt, having an emission range comprised between 250 and 370 nm and a peak of maximum intensity at 310 nm. The distance between the lamp and the Petri dish was about 30 cm. The time of such irradiation cycles was in the range of 15-90 min. For each polymeric concentration the time occurring to obtain hydrogels films easily detachable from the dish, has been determined.

The following Table 2 shows as example, the irradiation times necessary to obtain hydrogel films considering three different concentrations.

TABLE 2

| HA-EDA-MA concentration (w/v) | Time to form hydrogel films based on HA-EDA-MA |
|---|---|
| 2% | 60 min |
| 4% | 45 min |
| 8% | 20 min |

Example 8

Auto Crosslinking of Hyaluronic Acid-Hydrazine (HA-Hy)

HA-Hy derivative obtained as in Example 2 having a molar functionalization degree in hydrazine groups equal to 50% mol/mol was dissolved in distilled water to obtain a concentration equal to 1% w/v. The pH of the solution has been adjusted to 4.75 employing few drops of HCl 0.1 N.

A molar amount of (1-ethyl-3-(dimethylaminopropyl-carbodiimide) (EDCI) equal to the amount of hydrazine groups linked to HA was added and the pH has been maintained constant adding HCl 0.1 N until the formation of a hydrogel occurred. The hydrogel was recovered and washed in distilled water then freeze-dried.

The hydrogel weight yield was 80% compared to the starting polymer, the solid was then characterized by FT-IR analysis.

Example 9

Production of HA-EDA-BC Hydrogels

Figure 5:
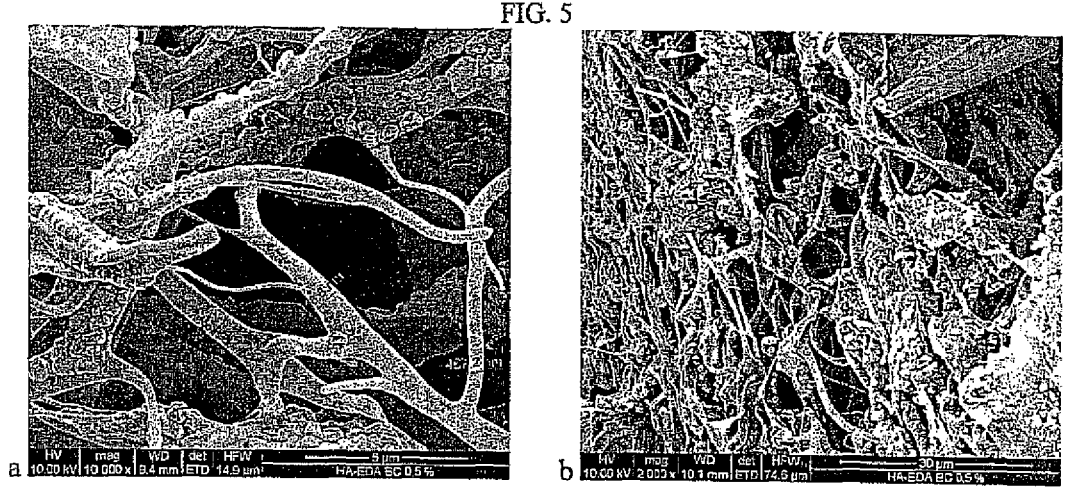
FIG. 5 shows SEM images of freeze-dried HA-EDA-BC hydrogel at 0.5% w/v.

Gel forming solution was obtained by dispersing the appropriate amount of polymer in Dulbecco phosphate buffer solution at pH 7.4 and then vortexing for 5 min until a complete solubilization was obtained. Hydrogels samples 0.5 w/v % based on HA-EDA-BC were prepared by air oxidation. After gel formation samples were washed with distilled water, and frozen in liquid nitrogen, freeze-dried and observed by using a scanning electron microscope. As showed in FIGS. 5a and 5b HA-EDA-BC hydrogel shows a fibrillar structure with interconnected fibrils ranging between 500 nm and 1 μm in diameter.

Example 10

Chondrocytes Encapsulation and Viability Assay

Human articular chondrocytes freshly isolated from human articular cartilage were cultivated for two passages during two weeks into complete DMEM. Freeze dried HA-EDA-BC was sterilized by UV irradiation (Using a 125 W UV lamp) for 2 h. Then 150 mg of HA-EDA-BC were dissolved in 9.4 ml of DMEM gently vortexing for about 10 min, then the foam formed was removed by sonication for 3 min. The chondrocytes encapsulation was accomplished adding 0.6 ml of DMEM containing $5 \times 10^6$ cells and gently shaking for few min to assure a homogeneous cells distribution. Then 150 μl of gel forming suspension were poured into NUNC CC-Inserts (polycarbonate membranes) Multidish 24 well. Gel forming hydrogel were then left for 2 h before to adding 1.1 ml of DMEM and incubating at 37° C., 5% of $CO_2$. Viability of encapsulated chondrocytes was evaluated by MTS assay after 2 h, 3, 7, 14 and 21 days. For each day, three inserts containing HA-EDA-BC encapsulated hydrogel were treated with 100 ml of MTS solution, and left to react for 4 h. Then absorbance was read in a 96 well plate at 550 nm (n=9) using as blank an empty HA-EDA-BC hydrogel treated as the hydrogel with the chondrocytes. Live and dead cytocompatibility assay was performed on HA-EDA-BC chondrocytes loaded hydrogel by employing a double staining procedure using calcein AM and ethidium homodimer-Ill (EthDIII). Calcein AM is a non-fluorescent, cell-permeant molecule that is cleaved inside the cell by intracellular esterases to yield its fluorescent counterpart (green fluorescence). EthD-III is a nucleic acid stain not permeable through viable cells but that can diffuse through the membrane of dead cells where it binds to the DNA and gives a red fluorescence. After three days of culture, inserts containing gels were washed three times with PBS pH 7.4 and then incubated for 1 h with the staining solutions and then washed again to remove the excess of staining solutions.

Gels were mounted on cover slips and analyzed using a Axioscop 2 fluorescence microscope (Zeiss) and captured with an Axiocam digital camera (Zeiss) interfaced with a computer.

Figure 6:
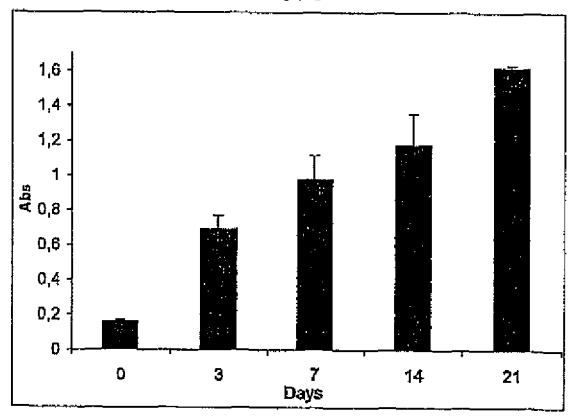
FIG. 6 shows proliferation of human chondrocytes encapsulated into HA-EDA-BC hydrogels. Value are expressed as absorbance±standard deviation (n=9).

As seen in FIG. 6, absorbance obtained by MTS analysis increases during all 21 days of incubation demonstrating a good viability and proliferation of the cells inside the three-dimensional hydrogel scaffold based on HA-EDA-BC.

Figure 7:
FIG. 7 shows live/dead staining of 3-D encapsulated chondrocytes into HA-EDA-BC hydrogels after 3 days of culture. Dead cells are indicated by the frames.

Live Dead fluorescence picture, see FIG. 7, after three days of culture shows several live cells and only few dead cells (see frames in the picture) thus indicating good biocompatibility of the encapsulating procedure. In the original colour picture, live cells are green and dead cells are red.

This invention has been described referring to some specific embodiments, but it is to be intended that obvious variations or modifications can be operated by experts in the field without exiting from the scope of protection.

The invention claimed is:

1. A functionalized derivative of hyaluronic acid having molecular weight in the range of from 50000 to 1500000 dalton obtainable from a process comprising the following subsequent steps:
    a) activation of at least one hydroxyl group of hyaluronic acid, in the form of a salt thereof soluble in organic solvents, by reaction of the said hyaluronic acid salt, in a polar aprotic solvent, with a carbonilating agent selected from carbonic phenyl esters and haloformic phenyl esters;
    b) reaction of the activated hyaluronic acid salt resulting from step a), through a nucleophilic substitution reaction with a compound of the general formula NH2-R, wherein R is selected from the group consisting of NH2, (CH2)2-NH2, a polyacrylic chain, a polyoxyethylene chain or a molecule of low molecular weight or a high molecular weight molecule.

2. The functionalized derivative according to claim 1 wherein the functionalization degree is comprised between at least one hydroxyl group and the whole hydroxyl groups of hyaluronic acid.

3. The functionalized derivative according to claim 1, wherein the said carbonilating agent is selected from bis(4 nitrophenylcarbonate) and chlorophenylcarbonate.

4. The functionalized derivative according to claim 1, wherein said hyaluronic acid salt is selected from tetrabutylammonium salt and cetyltrimethylammonium salt.

5. The functionalized derivative according to claim 1, wherein said polar aprotic solvent is selected from the group consisting of: dimethylsulphoxide, dimethylformamide, dimethylacetamide and their mixtures.

6. The functionalized derivative according to claim 1, wherein both steps of activation (a) and nucleophilic substitution (b) are carried out at a temperature comprised between 10° C. and 60° C.

7. A functionalized derivative for hydrogel production obtained subjecting the functionalized derivative of hyaluronic acid obtained according to claim 1 to a self-crosslinking in the presence of a carbodiimide as activating agent, or to chemical crosslinking by means of the use of bifunctional or polyfunctional crosslinking agents.

8. A functionalized derivative according to claim 1, obtained subjecting a functionalized derivative of hyaluronic acid in salt form obtained from said step b) to a further functionalization by nucleophilic substitution by reaction with a compound of formula Y—R', wherein Y is a good leaving group selected from halogen, N-oxysuccinimide, an alkoxyl with 1-6 carbon atoms, or Y represents the electrophilic portion of an anhydride or an epoxide, and R' is selected from the group consisting in:
    acryloyl or methacryloyl group both optionally substituted or a group belonging to a molecule, soluble in organic solvents or in aqueous solvents.

9. A functionalized derivative according to claim 8, wherein said further functionalization is carried out in aqueous medium or organic solvent, preferably a polar aprotic solvent selected from the group consisting of: dimethylsulphoxide, dimethylformamide, dimethylacetamide and their mixtures.

10. The functionalized derivative according to claim 8, wherein said further functionalization is carried out at a temperature comprised between 5° C. and 60° C.

11. The functionalized derivative according to claim 8, wherein said further functionalization is carried out in the presence of a catalyst selected from the group consisting of: diethylamine, triethylamine, dimethylaminopyridine and their mixtures.

12. The functionalized derivative according to claim 8, wherein said compound of formula Y—R' corresponds to methacrylic anhydride, methacryloyl chloride, acryloy chloride, glycidyl acrylate or glycidyl-methacrylate.

13. The functionalized derivative according to claim 8, wherein the said compound of the formula Y—R' corresponds to the N-oxysuccinimide ester or diester of N,N'-dibenzoyl-L-cystine or similar derivatives.

14. The functionalized derivative according to claim 13, wherein the derivative obtained from the said further functionalization is subjected to a reduction process to obtain a benzoyl-cysteine moiety.

15. A hydrogel obtained subjecting the functionalized derivative of hyaluronic acid according to claim 12 to a photocrosslinking process, wherein the concentration of the said functionalized derivative in aqueous or organic solution is comprised between 1% w/v and 20% w/v.

16. The hydrogel according to claim 15, obtained by irradiation with maximum wavelengths in the range of from 180 to 800 nm, in the presence or in the absence of a radical initiator with irradiation times variable from 5 min to 10 hours.

17. A hydrogel obtained by subjecting the functionalized derivative of hyaluronic acid according to claim 12 obtainable by an irradiation process with γ rays, microwaves or other ionizing radiations.

18. A hydrogel obtained by subjecting the functionalized derivative of hyaluronic acid according to claim 13 to a process of autooxidation in air.

19. Hydrogels obtained from the functionalized derivative of claim 7 produced in the form of nano- or microparticles, films, membranes, fibers and scaffolds.

20. The hydrogel of claim 15 produced in the form of nano- or microparticles, films, membranes, fibers and scaffolds.

* * * * *